(12) United States Patent
Teng

(10) Patent No.: US 11,075,002 B2
(45) Date of Patent: Jul. 27, 2021

(54) MEMORY IDENTIFICATION AND RECOVERY METHOD AND SYSTEM BASED ON RECOGNITION

(71) Applicant: Robert K F Teng, Norwalk, CA (US)

(72) Inventor: Robert K F Teng, Norwalk, CA (US)

( * ) Notice: Subject to any disclaimer, the term of this patent is extended or adjusted under 35 U.S.C. 154(b) by 248 days.

(21) Appl. No.: 16/141,940

(22) Filed: Sep. 25, 2018

(65) Prior Publication Data

US 2020/0035347 A1  Jan. 30, 2020

(51) Int. Cl.

| | | |
|---|---|---|
| *A61M 21/00* | (2006.01) | |
| *G16H 20/70* | (2018.01) | |
| *G16H 10/60* | (2018.01) | |
| *G06F 16/907* | (2019.01) | |
| *G06K 9/00* | (2006.01) | |
| *G06K 9/46* | (2006.01) | |
| *G06K 9/62* | (2006.01) | |
| *G06K 9/66* | (2006.01) | |
| *G06K 9/72* | (2006.01) | |
| *G10L 15/08* | (2006.01) | |
| *G10L 15/22* | (2006.01) | |

(52) U.S. Cl.
CPC ............ *G16H 20/70* (2018.01); *A61M 21/00* (2013.01); *G06F 16/907* (2019.01); *G06K 9/00288* (2013.01); *G06K 9/00718* (2013.01); *G06K 9/4638* (2013.01); *G06K 9/4676* (2013.01); *G06K 9/6227* (2013.01); *G06K 9/66* (2013.01); *G06K 9/726* (2013.01); *G10L 15/08* (2013.01); *G10L 15/22* (2013.01); *G16H 10/60* (2018.01); *A61M 2021/0016* (2013.01); *A61M 2021/0022* (2013.01); *A61M 2021/0027* (2013.01); *A61M 2021/0044* (2013.01); *A61M 2205/52* (2013.01); *G10L 2015/088* (2013.01)

(58) Field of Classification Search
CPC ....... A61M 21/00; G16H 20/70; G16H 10/60; G06K 9/00624; G06K 9/0063
See application file for complete search history.

(56) References Cited

U.S. PATENT DOCUMENTS

| | | | |
|---|---|---|---|
| 2018/0144189 A1* | 5/2018 | Tran ...................... | G06K 9/6256 |
| 2019/0164013 A1* | 5/2019 | Chen .................... | G06K 9/6256 |

* cited by examiner

*Primary Examiner* — John P Lacyk
(74) *Attorney, Agent, or Firm* — Raymond Y. Chan; David and Raymond Patent Firm

(57) ABSTRACT

The present invention is adapted for recognition technology improvement, which provides a memory identification and recovery method based on recognition, including: S1. collecting the data information from the scene of activity through a recognition device; S2. conducting salient feature extraction to the data information collected from the scene and generating feature marks; S3. building mapping relations between the generated feature marks and the extracted data information, automatically generating memory information in the database, and storing the information in the database; S4. inputting related data information for searching; S5. selecting a corresponding method to search the generated memory information in the database based on the input data information; S6. determining if there is related data information in the memory data. The method can helps to enhance memory of the user, recover memory after forget it, recover effectively through recognition technology, improve memory, and retrieve memory quickly after memory loss, which is convenient and efficient.

20 Claims, 1 Drawing Sheet

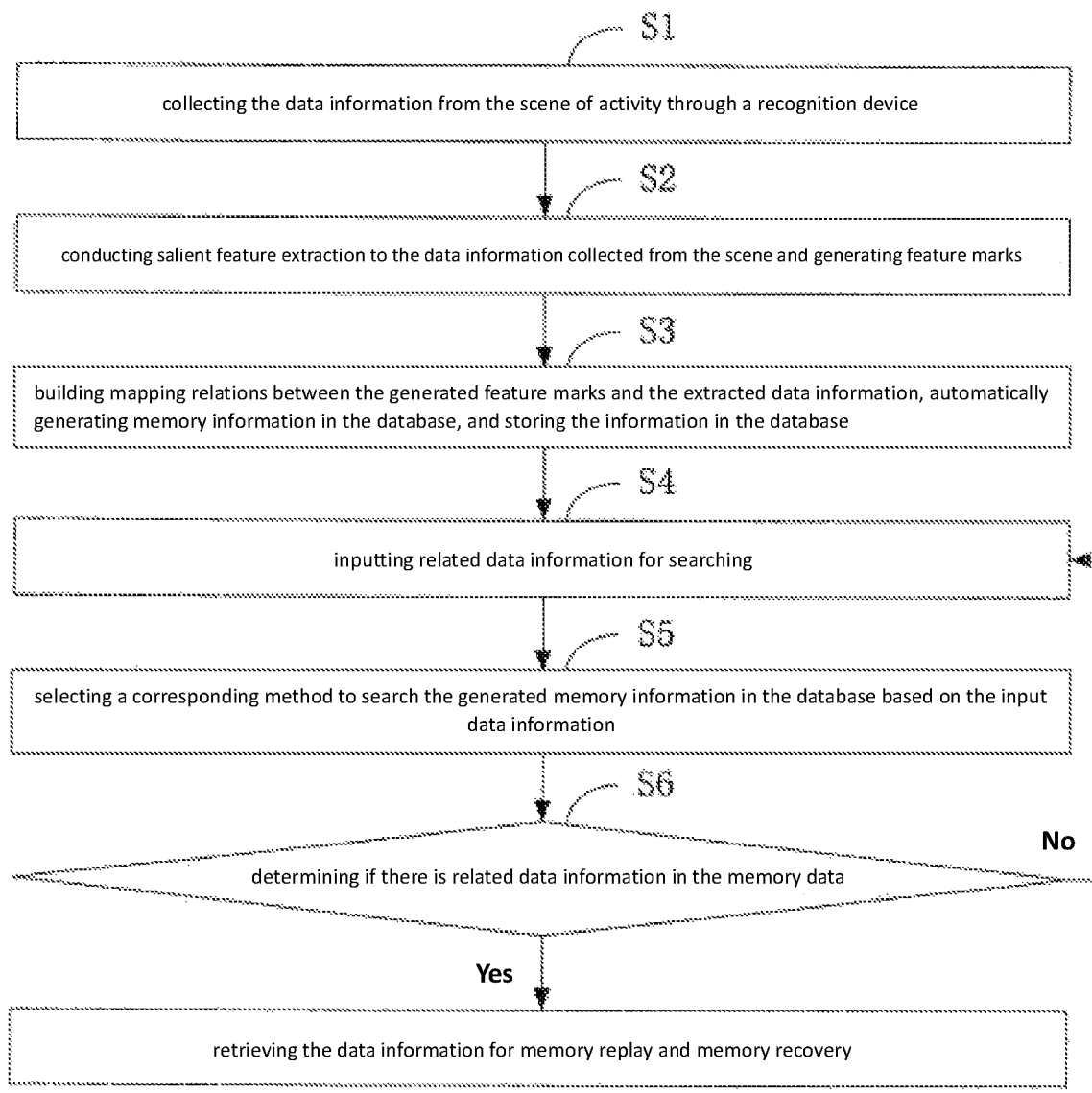

MEMORY IDENTIFICATION AND RECOVERY METHOD AND SYSTEM BASED ON RECOGNITION

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention is related to the field of recognition technology improvement, and more particularly, to a memory identification and recovery method based on recognition.

Description of Related Arts

The present invention is mainly to help in recovery from recognition and memory inability. Currently, most cases of memory inability are caused by Alzheimer disease, which is an insidious onset, progressive, and degenerative nervous system disease with symptoms of the comprehensive clinical manifestations of dysmnesia aphasia, apraxia, lost, visuospatial function deficits, executive dysfunction, and personality and behavior changes. The cause of the disease is unknown yet and the disease is commonly known as the geriatric disease.

The present invention may be implemented through wearable devices to help users with recognition and memory inability. It utilizes saliency detection, automatic semantic image data and shape segmentation, and etc. of artificial intelligence to recognize the user's memory automatically, conduct feature mark generation, and store persons, matters, scenes, and etc. for the memory, so as to retrieve the related persons, matters, scenes, and etc. of the memory according to the memory need of the user himself/herself or the other, which effectively helps the user to restore and recover his/her memory, overcome memory inabilities, enjoy a better quality of life.

The present invention may also be utilized for helping memory inability caused by other nervous system degenerative diseases, such as vascular diseases, frontotemporal diseases, Parkinson's disease, and etc. In addition, it may also be utilized for helping memory inability caused by traumatic brain injury, psychological amnesia, and etc.

SUMMARY OF THE PRESENT INVENTION

An object of the present invention is to provide a memory identification and recovery method based on recognition to solve the technical issues of memory loss and difficulty in recovery support.

The present invention can be implemented through a memory identification and recovery method based on recognition, comprising the steps of:

S1. collecting the data information from the scene of activity through a recognition device;

S2. conducting salient feature extraction to the data information collected from the scene and generating feature marks;

S3. building mapping relations between the generated feature marks and the extracted data information, automatically generating memory information in the database, and storing the information in the database;

S4. inputting related data information for searching;

S5. selecting a corresponding method to search the generated memory information in the database based on the input data information; and S6. determining if there is related data information in the memory data, and retrieving the data information for memory replay and memory recovery if there is or determining that the input information is beyond the information recorded in the database and returning to the step S4 if there is not.

Further technology of the present invention includes: feature marks is generated in the step S2 through a method selected from the group consisting of saliency detection, automatic semantic image segmentation, and combinations thereof.

Further technology of the present invention includes: the step S5 also comprises the step of:

S31. encrypting the memory information generated automatically and transmitting the encrypted memory information to a cloud for big data storage. Further technology of the present invention comprises: the step S6 also comprises the step of:

S61. reinforcing and updating the information of the subject stored in the memory in the database through learning after the corresponded memory recovery was confirmed.

Further technology of the present invention includes: the recognition device of the step S1 utilizes auditory sense, visual sense, gustatory sense, touch sense, and smell sense to sense the scene of activity and collect the data information.

Further technology of the present invention includes: the related memory data input in the step S4 comprises keyword, image, and voice for the information of self and others.

Further technology of the present invention includes: the search in the step S5 is conducted through a method selected from the group consisting of artificial intelligence interaction, deep learning, searching, novelty checking, finding, and combinations thereof.

Another object of the present invention is to provide a memory identification and recovery system based on recognition, comprising:

a scene acquisition unit, adapted for collecting the data information from the scene of activity through a recognition device;

a mark generation unit, adapted for conducting salient feature extraction to the data information collected from the scene and generating feature marks;

a mapping and storing unit, adapted for building mapping relations between the generated feature marks and the extracted data information, automatically generating memory information in the database, and storing the information in the database;

an input unit, adapted for inputting related data information for searching;

a search unit, adapted for selecting a corresponding method to search the generated memory information in the database based on the input data information; and a determination unit, adapted for determining if there is related data information in the memory data, and retrieving the data information for memory replay and memory recovery if there is or determining that the input information is beyond the information recorded in the database and returning to the input unit if there is not.

Further technology of the present invention includes: the mark generation unit generates feature marks through a method selected from the group consisting of saliency detection, automatic semantic image or data and shape segmentation, and combinations thereof.

Further technology of the present invention includes: the mapping and storing unit also comprises:

an encryption module, adapted for encrypting the memory information generated automatically and transmitting the encrypted memory information to a cloud for big data storage.

Further technology of the present invention includes: the mapping and storing unit also comprises:

a memory data updating module, adapted for reinforcing and updating the information of the subject stored in the memory in the database through learning after the corresponded memory recovery was confirmed.

Further technology of the present invention includes: the recognition device of the scene acquisition unit utilizes auditory sense, visual sense, gustatory sense, touch sense, and smell sense to sense the scene of activity and collect the data information;

the input unit utilizes input of keyword, image, and voice for related memory data for the information of self and others; and the search unit searches through a method selected from the group consisting of artificial intelligence, deep learning, searching, novelty checking, finding, and combinations thereof.

Advantages of the present invention includes that the method can helps to enhance memory of the user, recover memory after forget it, recover effectively through recognition technology, improve memory, and retrieve memory quickly after memory loss, which is convenient and efficient.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

FIG. 1 is a flow diagram of a memory identification and recovery method based on recognition according to a preferred embodiment of the present invention.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

FIG. 1 illustrates a flow diagram of a memory identification and recovery method based on recognition according to a preferred embodiment of the present invention, which comprises the following in detail. In step S1, it is to collect the data information from the scene of activity through a recognition device. Namely, a recognition device is utilized to collect data in the scene of the activity of the user. The content of the data being collected is various during the collection, which includes the environmental information of the scene, information of the surrounding subject(s), auditory information, information of the indicators, visual information, gustatory information, tactile information, smell information, information of the frequently appearing subjects, and etc. All types of information are composed based on the order of time in the collection process, so as to produce holistic data information.

In step S2, it is to conduct salient feature extraction to the data information collected from the scene and generate feature marks. That is, it utilizes a combination method of saliency detection and automatic semantic image or data and shape segmentation to mark on the collected data information and extract salient data, so as to generate special marks for the scene and activity. Alternatively, it may also utilize either saliency detection or the automatic semantic image segmentation to conduct the task directly, which includes extract the data and generate marks. Saliency detection and the automatic semantic image segmentation function is mainly according to the degree of human perceptions and the relations among the human perceptions. The human perceptions basically include detection of the movement of pupil, eyeball and muscle around eyes, vision of the eyes, auditory sense of the ears, smell sense of the nose, gustatory sense of the tongue, touch sense of the skin, and etc. The saliency or significance is determined according to the attention of the sense organs. For instance, it may detect movements, such as move and stop, of the eyes, including pupil, eyeball and muscle around eyes, so as to detect the salient substance to the perception of the eyes. When the salient substance and feeling are determined, it will utilize computer semantic image segmentation and computer semantic signal segmentation and identification to recognize them. Besides, other artificial intelligence marking method for recognition may also be utilized.

In step S3, it is to build mapping relations between the generated feature marks and the extracted data information, automatically generate memory information in the database, and store the information in the database. In other words, after the marks are generated, mapping relations will be built between the marks and the extracted data information in a one on one manner. Then the corresponding memory information will be automatically edited and stored in the database. The stored data information will be encrypted and upload to the cloud server for big data storage. This dual storage make the storing of the data safer and more stable.

In step S4, it is to input related data information for searching. That is, in order to recover a lost memory, it may input keywords or other regarding the characteristics of memory that the person wants to recover, so as to conduct a search. Besides, information of memory fragments of the other person may also be input and utilize for searching the mutual memory. Others like voice and image may also be utilized for searching the memory in the database.

In step S5, it is to select a corresponding method to search the generated memory information in the database based on the input data information. It may search the corresponded data information in the database in various forms. For example, it can search in the forms or ways of artificial intelligence, deep learning, searching, novelty checking, finding, and combinations of more than one of them so as to verify the results therebetween. In addition, the found data information can also be utilized for updating and learning.

Step S6. determining if there is related data information in the memory data, and retrieving the data information for memory replay and memory recovery if there is or determining that the input information is beyond the information recorded in the database and returning to the step S4 if there is not. It will update part of the content of the found data information when replaying it. The subject and other information in the memory will be compared and updated with those in the current information through the continuously reinforcement, such that the stored information can better store and preserve the memory and helps to strengthen and recall the memory.

The present invention also provides a memory identification and recovery system based on recognition, comprising:

a scene acquisition unit, adapted for collecting the data information from the scene of activity through a recognition device;

a mark generation unit, adapted for conducting salient feature extraction to the data information collected from the scene and generating feature marks;

a mapping and storing unit, adapted for building mapping relations between the generated feature marks and the extracted data information, automatically generating memory information in the database, and storing the information in the database;

an input unit, adapted for inputting related data information for searching;

a search unit, adapted for selecting a corresponding method to search the generated memory information in the database based on the input data information; and a determination unit, adapted for determining if there is related data information in the memory data, and retrieving the data information for memory replay and memory recovery if there is or determining that the input information is beyond the information recorded in the database and returning to the input unit if there is not.

The mark generation unit generates feature marks through a method selected from the group consisting of saliency detection, automatic semantic image segmentation, and combinations thereof.

The mapping and storing unit further comprises:

an encryption module, adapted for encrypting the memory information generated automatically and transmitting the encrypted memory information to a cloud for big data storage.

The determination unit further comprises:

a memory data updating module, adapted for reinforcing and updating the information of the subject stored in the memory in the database through learning after the corresponded memory recovery was confirmed.

The recognition device of the scene acquisition unit utilizes auditory sense, visual sense, gustatory sense, touch sense, and smell sense to sense the scene of activity and collect the data information, The input unit utilizes input of keyword, image, and voice for related memory data for the information of self and others, The search unit searches through a method selected from the group consisting of artificial intelligence interaction, deep learning, searching, novelty checking, finding, and combinations thereof.

The method can helps to enhance memory of the user, recover memory after forget it, recover effectively through recognition technology, improve memory, and retrieve memory quickly after memory loss, which is convenient and efficient.

The above is just a preferred embodiment of the present invention, which shall not limit the present invention. Any modification, equivalence, alternative, improvement, and etc. that is within the spirit and principle of the present invention shall be within the scope and extent of protection of the present invention.

One skilled in the art will understand that the embodiment of the present invention as shown in the drawing and described above is exemplary only and not intended to be limiting.

What is claimed is:

1. A method for memory identification and recovery based on recognition, the method comprising the steps of:
    (a) collecting one or more data information from a scene of activity of a user through a recognition device, wherein the one or more data information include one or more of an environmental information of the scene of activity, an information of a surrounding subject of the scene of activity, an auditory information of the scene of activity, an information of indicators of the scene of activity, a visual information of the scene of activity, a gustatory information of the scene of activity, a tactile information of the scene of activity, a smell information of the scene of activity, an information of frequently appearing subjects of the scene of activity, wherein the one or more data information are holistic data information collected based on an order of time during the collecting of the one or more data information from the scene of activity of the user;
    (b) conducting a salient feature extraction to the one or more data information collected from the scene of activity of the user to form one or more extracted data information and generating one or more feature marks for the scene of activity;
    (c) building mapping relations between the feature marks generated and the extracted data information, automatically generating a memory information in a database, and storing the memory information in the database as memory data;
    (d) searching for a lost memory by inputting one or more related data information in order to recover the lost memory from the memory data, wherein the one or more related data information include at least one of voice and image of the user, keywords, characteristics of a memory related to the memory information to be searched of the user, and information of memory fragments of a mutual person who has the memory with the user;
    (e) retrieving the corresponding data information for memory replay and memory recovery when the related data information is determined in the memory data; and
    (f) repeating the above step (d) when the one or more related data information inputted is determined not in the memory data.

2. The method, as recited in claim 1, wherein the step (b), which is conducted by a combination method selected from the group consisting of a saliency detection according to attention of sense organs of the user and an automatic semantic image and shape segmentation according to a degree of human perceptions and relations among the human perceptions, further comprises the steps of:
    (b1) marking on the data information collected and extracting data from the data information collected; and
    (b2) generating specific marks for the scene of activity.

3. The method, as recited in claim 1, wherein the step (b), which is conducted by a method selected from the group consisting of a saliency detection according to attention of sense organs of the user and an automatic semantic image segmentation according to a degree of human perceptions and relations among the human perceptions, further comprises the steps of:

(b1) extracting data from the data information collected; and (b2) generating specific marks for the scene of activity.

4. The method, as recited in claim 2, wherein the human perceptions include detection of movement of pupil of the user, eyeball and muscle around eyes of the user, vision of the eyes of the user, auditory sense of ears of the user, small sense of nose of the user, gustatory sense of tongue of the user, touch sense of skin of the user, wherein the saliency detection detects movements of the user, including at least move and stop of the pupil, the eyeball and muscle around the eye of the eye of the user, wherein when salient substance and feeling are determined, a computer semantic image segmentation and computer semantic signal segmentation and identification is utilized for recognition.

5. The method, as recited in claim 3, wherein the human perceptions include detection of movement of pupil of the user, eyeball and muscle around eyes of the user, vision of the eyes of the user, auditory sense of ears of the user, small sense of nose of the user, gustatory sense of tongue of the user, touch sense of skin of the user, wherein the saliency detection detects movements of the user, including at least move and stop of the pupil, the eyeball and muscle around the eye of the eye of the user, wherein when salient substance and feeling are determined, a computer semantic image segmentation and computer semantic signal segmentation and identification is utilized for recognition.

6. The method, as recited in claim 4, wherein the step (c) further comprises the steps of encrypting the memory information stored in the database.

7. The method, as recited in claim 5, wherein the step (c) further comprises the steps of encrypting the memory information stored in the database.

8. The method, as recited in claim 6, wherein the step (c) further comprises a step of uploading the memory information encrypted to a cloud server.

9. The method, as recited in claim 7, wherein the step (c) further comprises a step of uploading the memory information encrypted to a cloud server.

10. The method, as recited in claim 1, before the step (e), further comprising a step of selecting a searching method to search for the memory information generated in the database based on the one or more related data information inputted, wherein the searching method is elected from the group consisting of artificial intelligence, deep learning, novelty checking, finding, and combination thereof.

11. A computer implemented device for memory identification and recovery system based on recognition for a user, comprising:

a recognition device configured to recognize one or more data information from a scene of activity of the user, including one or more of an environmental information of the scene of activity, an information of a surrounding subject of the scene of activity, an auditory information of the scene of activity, an information of indicators of the scene of activity, a visual information of the scene of activity, a gustatory information of the scene of activity, a tactile information of the scene of activity, a smell information of the scene of activity, an information of frequently appearing subjects of the scene of activity, wherein the one or more data information are holistic data information collected based on an order of time during the collecting of the one or more data information from the scene of activity of the user;

a scene acquisition means for collecting the one or more data information from the scene of activity of the user through the recognition device;

a mark generation means for conducting a salient feature extraction to the one or more data information collected from the scene of activity of the user to form one or more extracted data information and generating one or more feature marks for the scene of activity;

a mapping and storing means for building mapping relations between the feature marks generated and the extracted data information, automatically generating a memory information in a database, and storing the memory information in the database as memory data; and an input and search means for inputting one or more related data information for searching a lost memory from the memory data, wherein the one or more related data information include at least one of voice and image of the user, keywords, characteristics of a memory related to the memory information to be searched of the user, and information of memory fragments of a mutual person who has the memory with the user, wherein when the related data information is determined in the memory data, the corresponding data information is retrieved for memory replay and memory recovery.

12. The device, as recited in claim 11, wherein when the related data information is determined beyond the memory information stored in the database, the user is allowed to input other related data information.

13. The device, as recited in claim 11, wherein the mark generation means extracts and generates the one or more feature marks by conducting a combination method selected from the group consisting of a saliency detection according to attention of sense organs of the user and an automatic semantic image and shape segmentation according to a degree of human perceptions and relations among the human perceptions, wherein the data information collected is marked and extracted to generate specific marks for the scene of activity.

14. The device, as recited in claim 11, wherein the marked generation means extracts and generates the one or more feature marks by conducting a method selected from the group consisting of a saliency detection according to attention of sense organs of the user and an automatic semantic image segmentation according to a degree of human perceptions and relations among the human perceptions, wherein the data information collected is extracted to generate specific marks for the scene of activity.

15. The device, as recited in claim 13, wherein the human perceptions include detection of movement of pupil of the user, eyeball and muscle around eyes of the user, vision of the eyes of the user, auditory sense of ears of the user, small sense of nose of the user, gustatory sense of tongue of the user, touch sense of skin of the user, wherein the saliency detection detects movements of the user, including at least move and stop of the pupil, the eyeball and muscle around the eye of the eye of the user, wherein when salient substance and feeling are determined, a computer semantic image segmentation and computer semantic signal segmentation and identification is utilized for recognition.

16. The device, as recited in claim 14, wherein the human perceptions include detection of movement of pupil of the user, eyeball and muscle around eyes of the user, vision of the eyes of the user, auditory sense of ears of the user, small sense of nose of the user, gustatory sense of tongue of the user, touch sense of skin of the user, wherein the saliency detection detects movements of the user, including at least move and stop of the pupil, the eyeball and muscle around the eye of the eye of the user, wherein when salient substance and feeling are determined, a computer semantic image segmentation and computer semantic signal segmentation and identification is utilized for recognition.

17. The device, as recited in claim 15, wherein the step (c) further comprises the memory information stored in the database is encrypted and uploaded to a cloud server.

18. The device, as recited in claim 16, wherein the step (c) further comprises the memory information stored in the database is encrypted and uploaded to a cloud server.

19. The device, as recited in claim 1, wherein the memory information generated in the database based on the one or more related data information inputted is search by means of the group consisting of artificial intelligence, deep learning, novelty checking, finding, and a combination thereof.

20. The device, as recited in claim 1, wherein the memory information generated in the database based on the one or more related data information inputted is search by means of the group consisting of artificial intelligence, deep learning, novelty checking, finding, and combination thereof.

* * * * *